(12) United States Patent
Ebinuma et al.

(10) Patent No.: US 7,198,890 B2
(45) Date of Patent: Apr. 3, 2007

(54) METHOD FOR QUANTITATIVELY DETERMINING HOMOCYSTEINE AND A REAGENT FOR QUANTITATIVE DETERMINATION OF HOMOCYSTEINE

(75) Inventors: Hiroyuki Ebinuma, Ryugasaki (JP);
Takami Sarashina, Naka-gun (JP);
Takuji Matsumoto, Ryugasaki (JP);
Masahiro Sekiguchi, Ryugasaki (JP);
Koji Ushizawa, Ryugasaki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 446 days.

(21) Appl. No.: 10/755,236

(22) Filed: Jan. 13, 2004

(65) Prior Publication Data

US 2005/0153385 A1    Jul. 14, 2005

(51) Int. Cl.
*C12Q 1/00*    (2006.01)
*C12N 9/00*    (2006.01)
*C07K 1/00*    (2006.01)

(52) U.S. Cl. .................. 435/4; 435/183; 530/350
(58) Field of Classification Search ............... 435/183, 435/4; 530/350
See application file for complete search history.

(56) References Cited

U.S. PATENT DOCUMENTS 5,985,540 A    11/1999    Tan et al.
5,998,191 A    12/1999    Tan et al.

FOREIGN PATENT DOCUMENTS

| EP | 1 143 244 | 10/2001 |
|---|---|---|
| JP | 3-272688 | 12/1991 |
| JP | 2000-166597 | 6/2000 |
| JP | 2000-270895 | 10/2000 |
| JP | 2000-513589 | 10/2000 |
| JP | 2000-338096 | 12/2000 |
| JP | 2002-10787 | 1/2002 |
| JP | 2002-360295 | 12/2002 |
| WO | WO 03/044220 | 5/2003 |

OTHER PUBLICATIONS

M. Orlowski, et al., Biochemistry, vol. 10, No. 3, pp. 372-380, "Isolation of Highly Purified y-Glutamylcysteine Synthetase From Rat Kidney", 1971.
K. Yamaguchi, et al., J. Biochem., vol. 83, No. 2, pp. 479-491, "Rat Liver Cysteine Dioxygenase (Cysteine Oxidase)", 1978.
V. Kumar, et al., Biochemistry, vol. 22, pp. 762-768, "Purification and Characterization of a Cysteine Dioxygenase From the Yeast Phase of Histoplasma Capsulatum", 1983.
K. P. McCann, et al., Biochimica et Biophysica Acta, vol. 1209, pp. 107-110, "Human Cysteine Dioxygenase Type I: Primary Structure Derived From Base Sequencing of cDNA", 1994.
Sambrook Fritsch Maniatis, Molecular Cloning, A Laboratory Manual, Second Edition, pp. 1.6-1.81, 5.11-5.13, 16.2-16.55, 17.2-17.41, A1-A13 and F.1-F.11, "Cold Spring Harbor Laboratory Press", 1989.
H. Ozaki, et al., J. Biochem., vol. 91, No. 4, pp. 1163-1171, "Methionine Biosynthesis in Brevibacterium Flavum: Properties and Essential Role of O-Acetylhomoserine Sulfhydrylase", 1982.
S. Yamagata, J. Biochem., vol. 96, No. 5, pp. 1511-1523, "O-Acetylhomoserine Sulfhydrylase of the Fission Yeast Schizosaccharomyces Pombe: Partial Purification, Characterization, and its Probable Role in Homocysteine Biosynthesis", 1984.
J. Brzywczy, et al., Acta Biochimica Polonica, vol. 40, No. 3, pp. 421-428, "Comparative Studies on O-Acetylhomoserine Sulfhydrylase: Physiological Role and Characterization of the *Aspergillus nidulans* Enzyme", 1993.
V. Ducros, et al., Journal of Chromatography B, vol. 781, No. 1-2, XP-004394155, pp. 207-226, "Methods for Homocysteine Analysis and Biological Relevance of the Results", Dec. 5, 2002.

*Primary Examiner*—Mark Navarro
(74) *Attorney, Agent, or Firm*—Oblon, Spivak, McClelland, Maier & Neustadt, P.C.

(57) ABSTRACT

The present invention provides a method for quantitatively determining homocysteine in a biological specimen containing homocysteine and cysteine by use of an enzyme which is capable of forming hydrogen sulfide both from homocysteine and from cysteine, which comprises (a) reacting the biological specimen with cysteine dioxygenase in the absence of a reducing agent, (b) subsequently reacting the resultant specimen of (a) with a reducing agent and the enzyme which is capable of forming hydrogen sulfide both from homocysteine and from cysteine, and (c) measuring the concentration of the hydrogen sulfide thus obtained to determine the homocysteine concentration in the biological specimen; and a reagent for such a quantitative determination of homocysteine.

16 Claims, 1 Drawing Sheet

[Fig. 1]
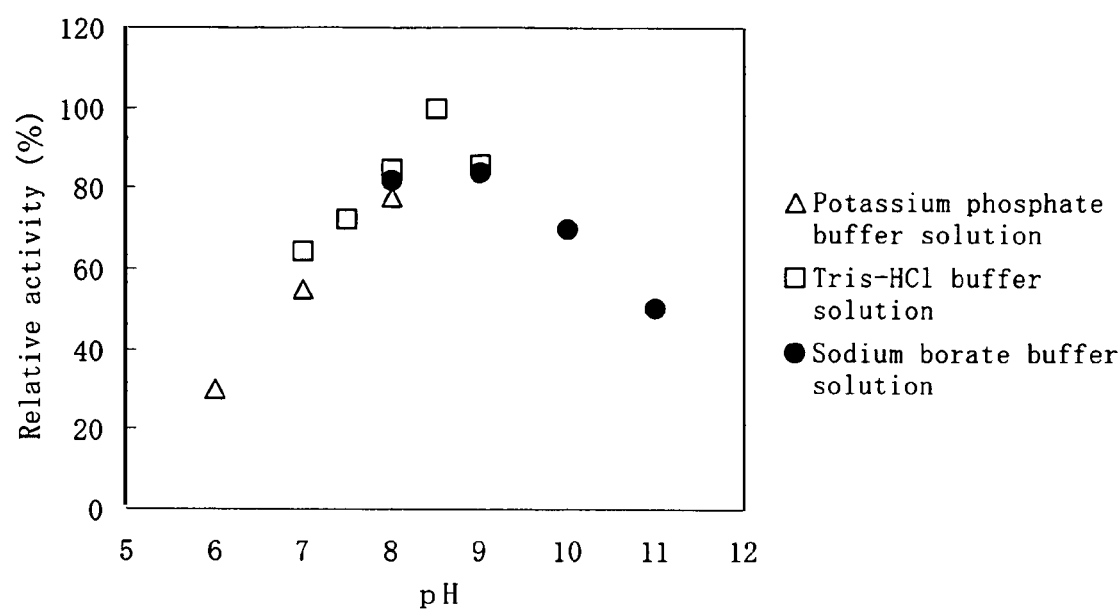

METHOD FOR QUANTITATIVELY DETERMINING HOMOCYSTEINE AND A REAGENT FOR QUANTITATIVE DETERMINATION OF HOMOCYSTEINE

FIELD OF THE INVENTION

The present invention relates to a method for quantitatively determining homocysteine wherein homocysteine in a biological specimen containing homocysteine and cysteine can be measured simply and accurately by use of an enzyme without influence of cysteine, and a reagent for such a quantitative determination of homocysteine.

BACKGROUND ART

As a method for quantitatively determining homocysteine in a specimen, a method wherein the homocysteine is reacted with an enzyme and the formed hydrogen sulfide is measured, has been known. The enzyme used in this method is, for example, L-methionine-γ-lyase or homocysteine desulfhydrase. Further, the present inventors have found that o-acetylhomoserine-lyase (EC class 4.2.99), known as an enzyme involved in the amino acid biosynthesis, also can produce hydrogen sulfide by catalyzing γ-substitution reaction in the presence of a thiol compound, and reported that homocysteine can be quantitatively determined with this enzyme (see JP-A-2000-166597).

However, since these enzymes react not only with homocysteine but also with cysteine to form hydrogen sulfide, there is a problem that it is difficult to measure accurate homocysteine concentration in a specimen wherein homocysteine and cysteine coexist (for example, a biological specimen such as blood).

Then, the present inventors proposed a method wherein, while the relation between known cysteine content of a starting solution and the amount of hydrogen sulfide resulting from a reaction with the above enzyme is preliminarily formulated, a specimen containing cysteine and homocysteine is reacted with said enzyme under a predetermined condition to measure the amount of formed hydrogen sulfide (1), and then the amount of hydrogen sulfide (2) that is derived from cysteine contained in said biological specimen and estimated, by calculation with the above formula, from a separately determined cysteine content in said biological specimen, is subtracted from the amount of hydrogen sulfide in (1) to determine the net content of homocysteine in the biological specimen wherein cysteine coexists (JP-A-2000-270895).

Further, Japanese International Publication No. 2000-513589 discloses a method wherein cysteine in a biological specimen is pretreated by an enzyme (e.g. γ-glutamyl cysteine synthase, cysteine oxidase, cystathionine β synthase or cysteine tRNA synthase) which is capable of converting it to a compound which is not a substrate of homocysteinase, and wherein the remaining homocysteine is measured with homocysteinase.

However, the method as disclosed in JP-A-2000-270895 is not a simple method since the cysteine content must be determined separately.

On the other hand, the method as disclosed in Japanese International Publication No. 2000-513589 has the following problems.

For example, the γ-glutamyl cysteine synthase (derived from rat kidney) has low substrate specificity, and may react not only with cysteine but also with cysteine derivatives or DL-homocysteine (see Biochemistry, 10(3), 1971; 372–380).

Further, although the cystathionine β synthase is known to be capable of undergoing a β-substitution reaction toward cysteine in the presence of a thiol compound, it can not be used for a method wherein homocysteine concentration is estimated by measuring the amount of formed hydrogen sulfide resulting from a reaction of homocysteine with an enzyme, because it produces hydrogen sulfide as product.

Moreover, since the cysteine tRNA synthase uses RNA as the substrate, there is a problem that it is susceptible to RNase.

Furthermore, cysteine dioxygenase derived from rat liver (another name: cysteine oxidase) has problems, for example, (1) it is necessary to have the enzyme incubated in the presence of cysteine under an anaerobic condition in order to convert it to an active form, (2) since it is very unstable and tends to be inactivated, its storage is difficult without a stabilizing protein (Protein-A) (see J. Biochem. 83(2), 1978; 479–491), and (3) it is easily inactivated in the presence of a reducing agent.

Accordingly, it is difficult to eliminate the cysteine in the specimen simply and efficiently by the methods disclosed in the above-mentioned patent publications.

Further, Japanese International Publication No. 2000-513589 discloses methionine γ-lyase derived from *Trichomonas vaginalis*, of which the substrate specificity toward homocysteine is enhanced by introducing mutation. JP-A-2002-10787 discloses o-acetylhomoserine sulfhydrase which is one of the enzymes involved in the amino acid biosynthesis derived from *Thermus thermophilus*, as an enzyme which does not substantially react with cysteine and specifically reacts with homocysteine. However, since there is a case where the cysteine concentration in the biological specimen is considerably high exceeding 1 mM, the use of such enzyme having improved substrate specificity is not sufficient to avoid the influence of cysteine completely.

SUMMARY OF THE INVENTION

Accordingly, it is an object of the present invention to provide a method wherein, in a quantitative determination of homocysteine in a biological specimen containing homocysteine and cysteine by use of an enzyme which is capable of forming hydrogen sulfide both from homocysteine and from cysteine, the influence of the coexisting cysteine can be avoided, by which simpler and more accurate quantitative determination of homocysteine can be carried out; and a reagent for quantitative determination of homocysteine which can be substantially applied to a clinical use, etc.

In order to accomplish the above object, the present invention provides a method for quantitatively determining homocysteine in a biological specimen containing homocysteine and cysteine by use of an enzyme which is capable of forming hydrogen sulfide both from homocysteine and from cysteine, which comprises (a) reacting the biological specimen with cysteine dioxygenase in the absence of a reducing agent, (b) combining the reducing agent and the enzyme which is capable of forming hydrogen sulfide both from homocysteine and from cysteine into said reaction mixture, and (c) measuring the concentration of the hydrogen sulfide formed in this manner to determine the homocysteine concentration in the biological specimen.

According to the present invention, by reacting the biological specimen with cysteine dioxygenase in the absence of a reducing agent, the free cysteine in the specimen is efficiently eliminated at first, and then by reacting it with a reducing agent, cysteines and homocysteines bound to proteins are liberated from the proteins, and the newly formed free cysteines can be eliminated by residual activity of the cysteine dioxygenase. Accordingly, with simultaneous use of a reducing agent, the reaction of an enzyme, which is capable of forming hydrogen sulfide both from homocysteine and from cysteine, is hardly influenced by the cysteine content of the specimen, so that hydrogen sulfide would be formed exclusively from the reaction of said enzyme with homocysteine, whereby the homocysteine in the specimen can be quantitatively determined simply and accurately by measuring the concentration of the formed hydrogen sulfide.

It is preferred that the reaction (a) is carried out in a buffer solution with pH of 5.5 to 7. According to this embodiment, the activity of cysteine dioxygenase can be maintained high, and it is thereby possible to eliminate the cysteine in the specimen efficiently.

It is preferred that the reducing agent is a thiol compound. According to this embodiment, cysteines and homocysteines bound to the proteins in the specimen can be efficiently liberated from the proteins, and it is thereby possible to reduce the influence of cysteine by the action of cysteine dioxygenase, so as to perform quantitative determination of homocysteine accurately.

It is preferred that the enzyme which is capable of forming hydrogen sulfide both from homocysteine and from cysteine is one of the enzymes involved in the amino acid biosynthesis. According to this embodiment, by reacting the homocysteine with one of the enzymes involved in the amino acid biosynthesis in the presence of the thiol compound, hydrogen sulfide can be formed efficiently by γ-substitution reaction.

It is preferred that the concentration of the formed hydrogen sulfide is measured with metal ions and a metal indicator. According to this embodiment, the concentration of the formed hydrogen sulfide can be quantitatively determined simply and accurately.

It is preferred that the cysteine dioxygenase is stored in a buffer solution with pH of 5.5 to 7 before the reaction (a). According to this embodiment, since the stability of the cysteine dioxygenase can be improved, the cysteine dioxygenase keeping its activity sufficiently higher can be used, whereby the cysteine can be eliminated efficiently.

It is preferred that the cysteine dioxygenase is cryopreserved in a buffer solution with pH of 5.5 to 7 containing sodium chloride or ammonium sulfate before the reaction (a). According to this embodiment, cysteine dioxygenase keeping its activity higher can be used.

It is preferred that the cysteine dioxygenase is lyophilized in a buffer solution with pH of 5.5 to 7 containing sodium chloride or ammonium sulfate and a sugar, in which cysteine dioxygenase is dissolved, before the reaction (a). According to this embodiment, cysteine dioxygenase keeping its activity still higher can be used.

The present invention also provides a set of reagents for quantitative determination of homocysteine, which comprises a reagent (I) containing cysteine dioxygenase, a reagent (II) containing a reducing agent and an enzyme which is capable of forming hydrogen sulfide both from homocysteine and from cysteine, and a reagent (III) containing metal ions and a metal indicator.

According to the present invention, it is possible to provide a reagent for quantitative determination, by which the influence of the cysteine coexisting in the specimen can be avoided and homocysteine can be quantitatively determined more simply and accurately, and which can be applied to the clinical use, etc.

It is preferred that the reducing agent is a thiol compound. According to this embodiment, it is possible to provide a reagent by which cysteines and homocysteines bound to the proteins in the specimen can be efficiently liberated from the proteins, which makes it possible to reduce the influence of cysteine in conjunction with the action of cysteine dioxygenase, so as to perform quantitative determination of homocysteine more accurately.

It is preferred that the enzyme which is capable of forming hydrogen sulfide both from homocysteine and from cysteine is one of the enzymes involved in the amino acid biosynthesis. According to this embodiment, by reacting the homocysteine with one of the enzymes involved in the amino acid biosynthesis in the presence of the thiol compound, hydrogen sulfide can be formed efficiently by γ-substitution reaction, whereby the construction of the reagent can be simplified.

It is preferred that the reagent (I) is obtained by dissolving cysteine dioxygenase in a buffer solution with pH of 5.5 to 7. According to this embodiment, the storage stability of cysteine dioxygenase can be improved.

It is preferred that the reagent (I) is obtained by dissolving cysteine dioxygenase in a buffer solution with pH of 5.5 to 7 containing sodium chloride or ammonium sulfate, and cryopreserving it. According to this embodiment, the storage stability of cysteine dioxygenase can be further improved.

It is preferred that the reagent (I) is obtained by dissolving cysteine dioxygenase in a buffer solution with pH of 5.5 to 7 containing sodium chloride or ammonium sulfate and a sugar, and lyophilizing it. According to this embodiment, the storage stability of cysteine dioxygenase can be still further improved.

BRIEF DESCRIPTION OF THE DRAWINGS

FIG. 1 is a graph showing the results of measurement in which the enzyme activity of cysteine dioxygenase in active form was assayed.

DETAILED DESCRIPTION OF THE INVENTION

Hereinafter, the procedure in the present invention for quantitative determination of homocysteine will be described stepwise.

(a) Step of Reacting the Biological Specimen with Cysteine Dioxygenase in the Absence of a Reducing Agent In this step, the cysteine dioxygenase is allowed to act on the biological specimen containing cysteine and homocysteine for a predetermined time in the absence of the reducing agent to selectively eliminate free cysteine. The enzyme reaction is preferably carried out usually at 20 to 50° C., more preferably at 25 to 37° C., for 1 to 30 minutes.

In the present invention, in a way where cysteine dioxygenase is applied to the biological specimen in the absence of the reducing agent, it is possible to prevent inactivation of cysteine dioxygenase and eliminate free cysteine efficiently.

In the present invention, some examples of the biological specimen containing homocysteine and cysteine are blood, serum, plasma and urine.

The cysteine dioxygenase used in the present invention is an enzyme which is capable of oxidizing cysteine to form cysteine sulfinic acid, and which is known to be derived from the mammalian livers (human, rats, etc.) or from

*Histoplasma capsulatum*. The cysteine dioxygenase is prepared from the above organisms by a known procedure as described in, for example, J. Biochem. 83(2), 1978; 479–491, Biochemistry 22, 1983; 762–768, etc.

Further, the cysteine dioxygenase gene has already been cloned (see JP-A-3-272688, and Biochimica Biophysica Acta 1209, 1994; 107–110), and its protein can be produced by the expression of recombinant cysteine dioxygenase gene.

For example, the cloned cysteine dioxygenase gene is incorporated into an appropriate expression vector by a known procedure, this expression vector is introduced into appropriate host cells to obtain a transformant, this transformant is cultured in an appropriate nutrient medium, and cysteine dioxygenase is obtained from this culture by extraction and purification (Molecular Cloning, A laboratory manual. 2nd Edition, 1989, Cold Spring Harbor Laboratory Press). As the host cells, *Escherichia coli, Bacillus subtilis*, yeast, zooblast, etc. may be mentioned. Further, for example, in case microorganisms such as *Escherichia coli* are used including the expression vector pUC, pMal, pQE vector (expression system of QIA express), etc. may be mentioned.

The extraction and purification of cysteine dioxygenase from the culture may be carried out by a known method, which for example comprises: an extraction method for cysteine dioxygenase such as sonication, treatment with a surfactant and/or enzymatic digestion; and a purification method for the extract thus obtained such as ion exchange chromatography, hydrophobic chromatography, affinity chromatography, gel filtration and/or isoelectric focusing.

Here, cysteine dioxygenase is very unstable, and when iron atoms in the enzyme molecules of this enzyme are detached, iron atoms are newly taken into the enzyme molecule by allowing iron ions to coexist (specifically, a compound which liberates iron ions, such as iron chloride, iron acetate or iron sulfate), and the enzyme activity can be recovered by further carrying out a heat treatment in the coexistence of a compound having a SH group (L-cysteine, cysteamine, dithiothreitol, mercaptoethanol, etc.) under anaerobic condition.

The amount of the enzyme to be added to a reaction mixture might be appropriately determined, depending upon the biological specimen to be applied to, such that the total cysteine contained in the biological specimen to be measured can sufficiently be eliminated. It is preferably 0.1 to 500 units (U)/ml, more preferably 1 to 50 units (U)/ml. One unit (U) of cysteine dioxygenase is defined as the enzyme activity that consumes 1 μmol of oxygen per minute under the following condition.

To a reaction cell maintained at 37° C., 0.9 ml of a 200 mM Tris-HCl buffer solution (pH 8.5) and 0.1 ml of a 100 mM L-cysteine are added, followed by preliminary incubating. And, an appropriate amount (about 5 μl) of an enzyme liquid is added thereto, and the reduction of dissolved oxygen in the solution is monitored with a dissolved oxygen meter to measure the consumed amount of oxygen.

In the present invention, it is preferred to conduct the enzyme reaction in a buffer solution with pH of 5.5 to 7, in order to prevent inactivation of cysteine dioxygenase during the reaction. It is thereby possible even for the step (b) which is described below to maintain the activity of cysteine dioxygenase sufficient enough, so as to eliminate the cysteine liberated by the reducing agent.

Further, in order to keep the activity of a cysteine dioxygenase as high as possible, it is preferred to use cysteine dioxygenase which is (1) stored by cooling in a buffer solution with pH of 5.5 to 7, (2) cryopreserved in a buffer solution with pH of 5.5 to 7 containing either sodium chloride or ammonium sulfate and subsequently thawed before use, or (3) dissolved in a buffer solution with pH of 5.5 to 7 containing either sodium chloride or ammonium sulfate and a sugar, and then lyophilized, having them reconstituted in water before use.

The above buffer solution is not particularly limited as long as it has a buffer capacity within a pH range of 5.5 to 7. For example, imidazole-HCl, acetate-NaOH, MES-NaOH buffer solutions, etc. may be mentioned. Further, the sugar is not particularly limited as long as it is capable of preventing insolubilization when the lyophilized enzyme agent is reconstituted. In particular, sucrose is preferred.

(b) Step of Reacting the Biological Specimen with the Reducing Agent and an Enzyme which is Capable of Forming Hydrogen Sulfide Both from Homocysteine and from Cysteine, to Form Hydrogen Sulfide The reducing agent is added to a reaction solution of the above step (a) to liberate cysteine bound to proteins which is not eliminated by the above step (a), and at the same time, homocysteine bound to proteins is liberated from the proteins, whereby the homocysteine in the specimen is completely liberated. And, while removing the liberated cysteine by residual activity of the cysteine dioxygenase, hydrogen sulfide is formed from homocysteine by an enzyme which is capable of forming hydrogen sulfide both from homocysteine and from cysteine, and simultaneously added with the reducing agent.

In the present invention, the cysteine dioxygenase is hardly inactivated in the step (a), and even in the presence of the reducing agent, the enzyme activity can be maintained at a level sufficient enough to eliminate the newly formed free cysteines, whereby cysteine can be eliminated efficiently. As a result, homocysteine can be allowed to act on the enzyme which is capable of forming hydrogen sulfide both from homocysteine and from cysteine without the influence of cysteine, and by measuring the concentration of the formed hydrogen sulfide, homocysteine in the specimen can be quantitatively determined simply and accurately.

As the enzyme used in the present invention, which is capable of reacting both with homocysteine and with cysteine to form hydrogen sulfide, is preferably an enzyme having a catalytic action of forming hydrogen sulfide by a substitution reaction in the presence of a reducing agent. As the enzyme, the enzymes involved in the amino acid biosynthesis such as o-acetylhomoserine-lyase, L-methionine γ-lyase and the like may, for example, be mentioned.

For example, o-acetylhomoserine-lyase is an enzyme having an ability to produce amino acids (e.g. activities with which homocysteine and acetic acid are formed from o-acetylhomoserine and hydrogen sulfide, or methionine and acetic acid are formed from o-acetylhomoserine and methanethiol), and when this enzyme is reacted with homocysteine, a catalytic action of forming hydrogen sulfide by γ-substitution reaction is observed (see JP-A-2000-166597).

Further, L-methionine γ-lyase is known to be an enzyme which shows a degradation (liberation) action to homocysteine in the absence of a thiol compound and forms hydrogen sulfide, but catalyzes γ-substitution reaction in the presence of a thiol compound.

In the present invention, one of the enzymes involved in the amino acid biosynthesis (o-acetylhomoserine-lyase) is particularly preferably used. o-Acetylhomoserine-lyase can be prepared by a known method from various microorganisms which produce it (for example, genus *Bacillus* as bacteria, genus *Saccharomyces* as yeast, and genus *Neurospora* as fungus), etc. (Ozaki et al., J. Biochem. 91; 1163–1171 (1982), Yamagata, J. Biochem. 96; 1511–1523 (1984), Brzywczy et al., Acta. Biochimica. Polonica. 40(3); 421–428 (1993)). Further, some types of o-acetylhomoserine-lyase are commercially available. For example, o-acetylhomoserine-lyase derived from *Bacillus* genus is available from Unitika Ltd. (under the trade name "GCS"), etc.

The amount of the enzyme, which is capable of reacting both with homocysteine and with cysteine to form hydrogen sulfide, to be added to a reaction mixture, is appropriately determined, depending upon the biological specimen to be measured in such an amount as is sufficient to the amount of the homocysteine in the biological specimen. It is preferably 0.01 to 100 units (U)/ml, more preferably 0.1 to 10 units (U)/ml. Here, one unit (U) of the enzyme is defined as enzyme activity that forms 1 μmol of hydrogen sulfide per minute under the following condition.

To 0.25 ml of a 200 mM Tris-HCl buffer solution (pH 8.5), 0.125 ml of a 8 mM 2-mercaptoethanol and 0.1 ml of a 10 mM DL-homocysteine are added, then resulting mixture was incubated at 37° C. for 5 minutes. Subsequently, 0.025 ml of an liquid enzyme appropriately diluted was added to this solution, followed by incubation at 37° C. for 15 minutes, and then 0.1 ml of a 3% NaOH aqueous solution, 0.325 ml of a 16 mM N,N-dimethyl-p-phenylenediamine hydrochloride solution, and 0.075 ml of a 10 mM ferric chloride hydrochloric acid solution, are sequentially added, and the solution is left to stand at room temperature for 15 minutes, and then the absorbance at 670 nm is measured. From the molar absorption coefficient ($\epsilon$=15,000) of methylene blue under this condition, the amount of hydrogen sulfide formed by the enzyme reaction is calculated to determine the enzyme activity.

Further, as the reducing agent to be used in the present invention, a thiol compound, a phosphine compound, a borohydride compound, etc, may, for example, be mentioned. Among them, the thiol compound is preferred since it is capable of specifically reducing cysteines and homocysteines bound to proteins (disulfide linkage) and further conducting an enzyme reaction with one of the enzymes involved in the amino acid biosynthesis, etc.

The thiol compound is not particularly limited as long as it acts as a substrate for a substitution reaction with an enzyme. Specifically, methanethiol, 2-mercaptoethane, dithiothreitol, thioglycerol, cysteamine, etc. may be mentioned.

In the present invention, it is preferred that the reducing agent is added to a reaction mixture so that its concentration will be 1 to 50 mM.

(c) Step of Measuring the Concentration of the Formed Hydrogen Sulfide, by Which the Homocysteine Concentration in the Biological Specimen is Measured The method for measuring the concentration of the formed hydrogen sulfide in the above step (b) is not particularly limited. However, it is preferred to measure it with metal ions and a metal indicator from the viewpoints of convenience and accuracy. For example, the method as disclosed in JP-A-2000-338096 and the like may be mentioned.

Specifically, it is preferred that iron (III) ions are used as the metal ions, and iron (II) ions formed by reduction of the iron (III) ions with hydrogen sulfide (sulfide ions) are detected by use of a metal indicator which undergoes color development by the reaction with iron (II) ions, and then the absorbance is measured and the concentration of hydrogen sulfide is determined from a preliminary prepared calibration curve. Otherwise, the residual iron (III) ions are detected by use of a metal indicator which undergoes color development by the reaction with iron (III) ions, and then the absorbance is measured and the concentration of hydrogen sulfide is determined from a preliminary prepared calibration curve.

And, on the basis of the calibration curve obtainable from the relation between the concentration of homocysteine and the concentration of hydrogen sulfide formed in a predetermined time by reaction with the enzyme which is capable of reacting both with homocysteine and with cysteine to form hydrogen sulfide, the concentration of homocysteine in the biological specimen can be calculated from the concentration of hydrogen sulfide measured in this step.

Further, the compounds to supply iron (III) ions are not particularly limited as long as, specifically, they liberate iron (III) ions in an aqueous solution. For example, chelate compounds such as iron (III) monosodium ethylenediamine tetraacetate and iron (III) ammonium oxalate hydrate as well as an ionic compound of iron (III) chloride, iron (III) sulfide ammonium hydrate, etc. may be mentioned. Among them, iron (III) monosodium ethylenediamine tetraacetate is preferably used.

Further, when the above chelate compounds are used, it is preferred that an auxiliary agent having an ability of coordinating ligands around iron ions (for example, IDA (iminodiacetic acid), ADA (N-(2-acetamide) iminodiacetic acid), Bicine (N,N-bis(2-hydroxyethyl)glycine, etc.) coexists in a range of 0.01 to 10 mM.

Further, the metal indicator which is capable of reacting with either iron (II) ions or iron (III) ions to undergo color development is not particularly limited as long as it forms a complex with iron ions, and preferred is the one which shows higher sensitivity of color development when the complex is formed. For example, as the metal indicator which is capable of reacting with iron (II) ions to undergo color development, pyridylazo compounds and nitrosoaminophenol compounds may, for example, be mentioned. Specifically, as the pyridylazo compounds, sodium 2-(5-bromo-2-pyridylazo)-5-[N-n-propyl-N-(3-sulfopropyl) amino]phenol (trade name: "5Br-PAPS", hereinafter abbreviated as 5Br-PAPS), sodium 2-(5-nitro-2-pyridylazo)-5-[N-n-propyl-N-(3-sulfopropyl) amino]phenol (trade name: "Nitro-PAPS"), etc. may be mentioned. As the nitrosoaminophenol compounds, 2-nitroso-5-[N-n-propyl-N-(3-sulfopropyl)amino]phenol (trade name: "Nitroso-PSAP") and 2-nitroso-5-[N-ethyl-N-(3-sulfopropyl)amino]phenol (trade name: "Nitroso-ESAP"), etc. may preferably be mentioned.

As the metal indicator which reacts with iron (III) ions to undergo color development, for example, Feron, Calcichrome, Chromazurol B, Chromazurol S, Chromotropic acid, etc. may be mentioned.

These metal indicators are water-soluble, and have such a property that they undergo color development with high sensitivity by the formation of complexes with either iron (II) or (III) ions. As the above metal indicators, ones having various features are commercially available, and, for example, available from Dojindo Laboratories.

When the concentration of hydrogen sulfide is measured by use of iron ions and a metal indicator which is capable of reacting with iron ions to undergo color development, it is preferred that the specimen is pre-treated with an aluminum salt and/or a gallium salt in conjunction with a chelating agent which is specific to copper ions. By this embodiment, it is possible to avoid the influence of components coexisting in the biological specimen (serum copper, transferrin, etc.) and measure the concentration of hydrogen sulfide more accurately.

As the aluminum salt, aluminum chloride and aluminum nitrate may, for example, be mentioned. As the gallium salt, gallium nitrate and gallium sulfate may, for example, be mentioned. Further, as the chelating agent specific to copper ions, neocuproine, bathocuproine or salts thereof may, for example, be mentioned.

The aluminum salt and/or the gallium salt is usually added in such an amount that the concentration will be preferably 0.01 to 10 mM, more preferably 0.3 to 3 mM. Here, in order to prevent the formation of hydroxides of aluminum and gallium in the alkaline pH range, an organic acid such as tartaric acid, citric acid, malic acid or IDA (iminodiacetic acid) of an appropriate concentration may preferably be used together.

Further, the chelating agent specific to copper ions is usually added in such an amount that the concentration will be preferably 0.01 to 50 mM, more preferably 0.5 to 10 mM.

Then, the reagent in the present invention for quantitative determination of homocysteine will be described below.

The reagent in the present invention for quantitative determination of homocysteine comprises a reagent (I) containing cysteine dioxygenase, a reagent (II) containing a reducing agent and an enzyme which is capable of forming hydrogen sulfide both from homocysteine and from cysteine, and a reagent (III) containing metal ions and a metal indicator. By adding the respective reagents to the specimen sequentially, it is possible to avoid the influence of cysteine coexisting in the specimen and quantitatively determine homocysteine in the specimen more simply and accurately.

Reagent (I)

The form of the reagent (I) as a product is appropriately selected from solution, cryopreserved products, lyophilized products, etc. Here, since the stability of cysteine dioxygenase is low, it is preferred to prepare and store it as follows.

(1) In a case where it is in the form of solution, it is preferred that cysteine dioxygenase is dissolved in a buffer solution having the pH of 5.5 to 7, and stored at 2 to 10° C. The buffer solution is not particularly limited as long as it exhibits a buffer capacity in a pH range of 5.5 to 7, and imidazole-HCl, acetate-NaOH, MES-NaOH buffer solutions, etc. may, for example, be mentioned. By storing cysteine dioxygenase in such a buffer solution, it is possible to prevent inactivation of cysteine dioxygenase in cold storage.

(2) In a case where it is in the form of a cryopreserved product, it is preferred that cysteine dioxygenase is dissolved in the buffer solution of the above (1) having sodium chloride or ammonium sulfate further added, and then cryopreserved, and stored preferably at −30° C. or lower, more preferably at −80° C. or lower. Sodium chloride or ammonium sulfate is usually added in such an amount that the concentration will be preferably 0.1 to 2M, more preferably 0.25 to 1M. It is thereby possible to prevent the formation of insolubles when the product is thawed and further improve the storage stability.

(3) In a case where it is in the form of a lyophilized product, it is preferred that cysteine dioxygenase is dissolved in the buffer solution of the above (2) having a sugar further added, and then lyophilized, and stored preferably at 10° C. or lower. As the sugar, for example, sucrose, etc. may be mentioned. The sugar is added in such an amount that the concentration will be preferably 0.1 to 20 (w/v)%, more preferably 5 to 20 (w/v)%. By adding the sugar, it is possible to prevent the formation of insolubles when the product is reconstituted with water and further improve the storage stability.

In the present invention, the cryopreserved product is preferred and the lyophilized product is more preferred from the viewpoint of storage stability.

Reagent (II)

As the components of the reagent (II) i.e. the reducing agent and the enzyme which is capable of forming hydrogen sulfide both from homocysteine and from cysteine, the same ones as described in the above explanation about the method for quantitatively determining homocysteine may preferably be used.

Further, in addition to the above basic components, the reagent (II) preferably contains the above-mentioned aluminum salt and/or gallium salt, chelating agent specific to copper ions and organic acid such as tartaric acid, citric acid, malic acid or IDA (iminodiacetic acid) so that the influence of components coexisting in the biological specimen (serum copper, transferrin, etc.) and accurately measure the concentration of hydrogen sulfide when the concentration of hydrogen sulfide is measured with iron ions and a metal indicator which is capable of reacting with iron ions to undergo color development. Further, it is preferred to contain an auxiliary agent having an ability of coordinating ligands around iron ions.

The concentrations of the aluminum salt and/or gallium salt, chelating agent specific to copper ions, organic acid and auxiliary agent having an ability of coordinating ligands around iron ions, may appropriately be set depending upon the above-mentioned concentrations.

The reagent (II) is prepared by dissolving the above respective components in a buffer solution (pH 7.0 to 9.0) such as Tris-HCl buffer solution, and usually stored at 2 to 10° C.

Reagent (III)

As the components of the reagent (III) i.e. the metal ions and metal indicator, the same ones as described in the above-mentioned explanation about the method for quantitatively determining homocysteine may preferably be used.

The reagent (III) is prepared by dissolving a compound which liberates iron (III) ions in an aqueous solution and the metal indicator in e.g. distilled water or an appropriate buffer solution.

EXAMPLES

Hereinafter, the present invention will be described in further detail with reference to examples. However, it should be mentioned that the present invention is by no means restricted to them. Here, the measurement of activity of cysteine dioxygenase is conducted in accordance with the above-mentioned measurement method, in which the process of the consumption rate of dissolved oxygen in the solution, which is consumed with L-cysteine as a substrate, is monitored by use of a dissolved oxygen meter ("TD-650" model, manufactured by Toko Kagaku Kenkyusho).

Preparation Example (Preparation of Cysteine Dioxygenase)

(1) Preparation of cDNA Encoding Human Cysteine Dioxygenase

The cDNA encoding human cysteine dioxygenase was PCR-amplified with a pair of specific primers designated Sequence No. 1 (sense primer) and Sequence No. 2 (antisense primer) from a commercially available human liver cDNA library (manufactured by Invitrogen Co.), and cloned. The above-mentioned primers, which is based on the nucleotide sequence of human cysteine dioxygenase gene described in Biochimica Biophysica Acta 1209, 1994; 107–110, were synthesized by a conventional method.

TOYOBO KOD kit (trade name, manufactured by Toyobo Co., Ltd.) was employed in the PCR, in which a heating step at 95° C. for 2 minutes was followed by 30 cycles of reaction consisting of a denaturing step at 95° C. for 0.5 minute, an annealing step at 60° C. for 0.5 minute and an extension step at 68° C. for 1 minute.

Free Text of Sequence List

Sequence No. 1: a sense primer for PCR-amplification of a DNA fragment encoding human cysteine dioxygenase.

Sequence No. 2: an antisense primer for PCR-amplification of a DNA fragment encoding human cysteine dioxygenase.

The amplified DNA fragment thus obtained was digested by the restriction enzymes NcoI and BamHI, and purified with agarose gel electrophoresis, and then ligated into the cognate site of an expression vector pQE60 (manufactured by QIAGEN Inc.). Resulting recombinant plasmid was introduced by a conventional method into *Escherichia Coli* (JM109 strain).

(2) Preparation of Human Cysteine Dioxygenase (2-1) Culture of Recombinant *Escherichia Coli*

The *Escherichia Coli* cells having a recombinant plasmid introduced were spread onto the LB agar medium containing ampicillin (100 μg/ml). After incubation at 37° C. overnight to let colonies form, a single colony thereof was inoculated into 3 ml of LB medium containing ampicillin (100 μg/ml) and 0.2 (w/v)% of glucose, and then cultured at 37° C. overnight. 0.5 ml of this pre-culture medium was inoculated into 50 ml of the LB medium, and then cultured at 37° C. overnight. 40 ml of resultant culture medium was further inoculated into 4 liters of the LB medium having L-cysteine (10 mM) added to, and culture was started at 37° C. After being sure that the absorbance of the culture medium at 600 nm was around 0.8OD, IPTG (isopropyl β-D-thiogalactopyranoside) was added so that its final concentration would be 1 mM. The culture was continued for further 5 hours, and then the bacterial cells were collected.

(2-2) Isolation of Cysteine Dioxygenase from Recombinant *Escherichia Coli*

In this expression system, since a tag of histidine is fused to an expression protein (cysteine dioxygenase), nickel chelate affinity chromatography was used for purification.

The bacterial cells obtained from the above culture were suspended in a Tris-HCl buffer solution (20 mM, pH 8.0, contains 0.5M NaCl), and disrupted by ultrasonic treatment. The resultant was centrifuged at 10,000×g for 15 minutes, and the supernatant was recovered to obtain a cell-free extract.

A column was prepared by treating Chelating Sepharose FF (trade name, manufactured by Amersham Pharmacia Biotech K.K.) with a nickel sulfate solution so as to get nickel ions adsorbed thereto, and then removing excess nickel ions by washing with water, and further conducting equilibration with a Tris-HCl buffer solution (20 mM, pH 8.0, contains 0.5M NaCl). To this column, the above cell-free extract was loaded for adsorption, and then washing was carried out with the above buffer solution.

Then, non-specifically adsorbed impurities were washed out with a buffer having 50 mM of imidazole coexisted in the above buffer solution, and the aimed enzyme protein (cysteine dioxygenase) was eluted with an elution buffer having 200 mM of imidazole coexisted in the above buffer solution, and then the protein fractions were collected.

To the collected protein fractions, ammonium sulfate was added and dissolved so that it would be 70% saturation. This solution was left to stand at 4° C. overnight and centrifuged to recover the precipitates. The obtained precipitates were dissolved in a small amount of a Tris-HCl buffer solution (20 mM, pH 8.0), and further dialyzed with the above buffer solution.

In order to supplement the iron for the enzyme protein from which the iron ion was detached during affinity purification, the dialyzed solution was diluted with a Tris-HCl buffer solution (20 mM, pH 8.0) so that the protein concentration in the dialyzed solution would be about 5 mg/ml, and then a 10 mM ferrous chloride aqueous solution so that its final concentration would be 0.4 to 0.5 mM, and this solution was left to stand at 4° C. overnight.

And, the iron-incorporated enzyme solution was added to the Tris-HCl buffer solution (100 mM, pH 9.0) containing 10 mM cysteamine at a ratio of 1:9, and this system was converted to an anaerobic condition by deaeration under reduced pressure or nitrogen substitution, and then heated at 37° C. for about 30 minutes for activation of the enzyme.

And, ammonium sulfate was added to the activated enzyme solution and dissolved therein so that it would be 70% saturation. This solution was left to stand under ice cooling for about 1 hour, and then centrifuged to recover the precipitates so as to obtain an active form of cysteine dioxygenase.

(3) Characteristics of Active Form of Cysteine Dioxygenase

Optimum pH

The enzyme activity of the obtained active form of cysteine dioxygenase was measured by the above method except that potassium phosphate buffer solution (pH 6.0 to 8.0), Tris-HCl buffer solution (pH 7.0 to 9.0) or sodium borate buffer solution (pH 8.0 to 11.0) was used as the buffer solution for measurement of enzyme activity. The results are indicated in FIG. 1. From FIG. 1, it is found that the optimum pH is 8.0 to 9.0.

Measurement of Molecular Weight

As a result of calculation by SDS-PAGE electrophoresis, the molecular weight was about 25,000 Da.

Stability

In a buffer Solution Having pH of 8.0 to 9.0 as the optimum pH range, complete inactivation was observed after stored at 4° C. overnight, and the stability was extremely low.

Example 1

Study on Storage Stability of Active Form of Cysteine Dioxygenase

Study on Storage Condition of Active Form of Cysteine Dioxygenase in a Solution

An active form of cysteine dioxygenase was added to each of respective 100 mM buffer solutions as indicated in Table 1, and stored at 4° C., and then the enzyme activity was monitored at certain intervals. The results are also indicated in Table 1.

TABLE 1

| Buffer solution | pH | Residual activity of cysteine dioxygenase (%) | |
|---|---|---|---|
| | | 2 days passed | 6 days passed |
| Malate-NaOH | 6.0 | 67 | 33 |
| | 6.5 | 55 | 35 |
| Imidazole-HCl | 6.5 | 65 | 55 |
| | 7.0 | 62 | 38 |
| Acetate-NaOH | 5.5 | 20 | 0 |
| | 6.0 | 56 | 28 |
| | 6.5 | 72 | 44 |
| MES-NaOH | 6.0 | 47 | 11 |
| | 6.5 | 59 | 18 |
| | 7.0 | 26 | 5 |
| PIPES-NaOH | 6.5 | 38 | 14 |
| | 7.0 | 45 | 15 |
| ADA-NaOH | 6.0 | 0 | 0 |
| | 6.5 | 0 | 0 |
| | 7.0 | 0 | 0 |
| BisTris-NaOH | 6.0 | 17 | 0 |
| | 6.5 | 6 | 0 |
| | 7.0 | 0 | 0 |
| Tris-HCl | 8.5 | 0 | 0 |
| TAPS-NaOH | 8.5 | 0 | 0 |
| Bicine-NaOH | 8.5 | 0 | 0 |

From Table 1, it is found that the storage stability of the cysteine dioxygenase is remarkably improved by storing in a buffer solution having a buffer capacity in a pH range at around 5.5 to 7 (particularly maleic acid, imidazole, acetate buffer solution and, among Good's buffer solution, MES, PIPES, etc.). On the other hand, its storage stability was extremely low in the buffer solution of pH 8.5.

Study on Cryopreservation Condition

The active form of cysteine dioxygenase was added to a 20 mM imidazole-HCl buffer solution (pH 6.5) containing 0.5M of each of the respective salts as indicated in Table 2, and cryopreserved at $-30°$ C. for one day. Then, it was thawed at room temperature and the residual activity of enzyme was measured. The results are also indicated in Table 2. Here, in this table, "++" indicates insolubles observed, and "−" indicates no insolubles observed (hereinafter the same applies).

TABLE 2

| Type of salt added | Insolubles when thawed after cryopreservation | Residual activity of enzyme (%) |
|---|---|---|
| None | ++ | 0 |
| 0.5M NaCl | − | 96 |
| 0.5M KCl | ++ | 26 |
| 0.5M NH$_4$Cl | ++ | 14 |
| 0.5M (NH$_4$)$_2$SO$_4$ | − | 86 |
| 0.5M Na$_2$SO$_4$ | ++ | 0 |

From Table 2, it is clear that, by being with some salt, the residual activity of enzyme after a freeze-thawing cycle remains high. In particular, Table 2 shows that, by coexisting with either sodium chloride or ammonium sulfate, precipitation of enzyme proteins after a freeze-thawing cycle can be prevented and thus the residual activity of enzyme keeps very high.

Further, the active form of cysteine dioxygenase was added to a 20 mM imidazole-HCl buffer solution (pH 6.5) containing 0.5M of ammonium sulfate, and cryopreserved at $-30°$ C. or $-80°$ C. for 4 weeks. Then, it was thawed, and the residual activity of enzyme was measured. The results are indicated in Table 3.

TABLE 3

| | After 1 week | | After 2 weeks | | After 4 weeks | |
|---|---|---|---|---|---|---|
| | $-30°$ C. | $-80°$ C. | $-30°$ C. | $-80°$ C. | $-30°$ C. | $-80°$ C. |
| Residual activity of enzyme (%) | 71 | 88 | 65 | 108 | 60 | 93 |

From Table 3, it is clear that the enzyme activity can be maintained for a long time by cryopreservation (particularly at $-80°$ C.)

Study on the Conditions of Lyophilization

The active form of cysteine dioxygenase was added to a 20 mM imidazole-HCl buffer solution (pH 6.5) containing 0.5M of ammonium sulfate, and further sucrose was added so that the final concentration thereof would be 10 (w/v) %, and then lyophilized. The lyophilized product was dissolved in distilled water, of which volume is equal to that of the obtained solution before lyophilization, and the residual activity of enzyme was measured. As a control, the cysteine dioxygenase solution with no sucrose added was lyophilized in a same way as above. The results are indicated in Table 4.

TABLE 4

| | Residual activity of enzyme (%) | Insolubles when reconstituted |
|---|---|---|
| No sucrose added | 63 | ++ |
| Sucrose added | 87 | − |

From Table 4, it is clear that by allowing sucrose to coexist with, the enzyme activity is hardly inactivated by lyophilization, and also clear that precipitation of insolubles, when the product was reconstituted, can be prevented.

Example 2

Measurement of Homocysteine in the Coexistence of Cysteine

First, second and third reagents having the following compositions were prepared.

| First reagent: | |
|---|---|
| Active form of cysteine dioxygenase | 30 U/ml |
| Ammonium sulfate | 500 mM |
| Imidazole-HCl buffer solution | 20 mM (pH 6.5) |
| Second reagent: | |
| o-Acetylhomoserine-lyase (manufactured by Unitika Ltd., trade name: "GCS") | 0.7 U/ml |
| Thioglycerol | 10 mM |
| ADA (N-[2-acetamido]iminodiacetic acid) | 10 mM |
| Neocuproine | 2 mM |
| Gallium nitrate | 0.5 mM |
| Tartaric acid | 0.5 mM |
| Surfactant | 0.6% |
| Tris-HCl buffer solution | 132 mM (pH 8.5) |
| Third reagent: | |
| Fe (III) EDTA | 5.6 mM |
| Nitroso-PSAP (Dojindo Laboratories) | 2 mM |

For a specimen to be tested with above reagents, pooled serum was combined with solution containing varied amount of cystine, which is an oxidized form of cysteine, in the ratio 9:1, by volume, so that ones containing 0 to 500 µmol/L of cystine (which correspond to 0 to 1,000 µmol/L in terms of cysteine) were prepared, while measurement was carried out with Hitachi 7170 Automatic analyzer. Specifically, 35 µl of the first reagent was added to 14 µl of the specimen and left to stand at 37° C. for 2 minutes, and then 175 µl of the second reagent was added thereto and left to stand at 37° C. for 3 minutes. Further, 56 µl of the third reagent was added thereto and left to stand at room temperature for 5 minutes, and then the absorbance was measured at a wavelength of 750 nm. The results are shown in Table 5.

TABLE 5

| Cystine content (µmol/L) | Homocysteine concentration (µmol/L) |
|---|---|
| 0 | 18.9 |
| 100 | 19.8 |
| 200 | 20.4 |
| 300 | 20.8 |
| 400 | 22.1 |
| 500 | 21.5 |

From Table 5, it is obvious that, according to the present invention, the concentration of homocysteine, which is coexisting with high concentration of cysteine in a specimen, can be measured with little influence of cysteine. Further, it is suggested that the influence from oxidized form of cysteine, which is an actual form of cysteine in the biological specimen, also can be avoided without problem.

As mentioned above, according to the present invention, by reacting the biological specimen with cysteine dioxygenase in the absence of the reducing agent, free cysteine in the specimen can be efficiently eliminated, and then by reacting the specimen thus obtained with the reducing agent, cysteines and homocysteines bound to proteins can be liberated from the proteins, and the newly formed free cystines can be eliminated by residual activity of the cysteine dioxygenase. Accordingly, with simultaneous use of a reducing agent, the reaction of an enzyme, which is capable of forming hydrogen sulfide both from homocysteine and from cysteine, is hardly influenced by the cysteine content of the specimen, so that hydrogen sulfide would be formed exclusively from the reaction of said enzyme with homocysteine, whereby the homocysteine in the specimen can be quantitatively determined simply and accurately by measuring the concentration of the formed hydrogen sulfide.

Further, the storage stability of cysteine dioxygenase, which is generally low, can be improved by storing cysteine dioxygenase in a buffer solution of pH 5.5 to 7, which enables to provide a practically applicable reagent for quantitatively determining homocysteine for the clinical use.

absence of a reducing agent, (b) subsequently reacting the resultant specimen of (a) with a reducing agent and the enzyme which is capable of forming hydrogen sulfide both from homocysteine and from cysteine, and (c) measuring the concentration of the hydrogen sulfide thus obtained to determine the homocysteine concentration in the biological specimen.

2. The method for quantitatively determining homocysteine according to claim 1, wherein the reaction (a) is carried out in a buffer solution with pH of 5.5 to 7.

3. The method for quantitatively determining homocysteine according to claim 1, wherein the reducing agent is a thiol compound.

4. The method for quantitatively determining homocysteine according to claim 1, wherein the concentration of the formed hydrogen sulfide is measured with metal ions and a metal indicator.

5. The method for quantitatively determining homocysteine according to claim 1, wherein the cysteine dioxygenase is stored in a buffer solution with pH of 5.5 to 7 before the reaction (a).

6. The method for quantitatively determining homocysteine according to claim 1, wherein the cysteine dioxygenase is cryopreserved in a buffer solution with pH of 5.5 to 7 containing sodium chloride or ammonium sulfate before the reaction (a).

7. The method for quantitatively determining homocysteine according to claim 1, wherein the cysteine dioxygenase is lyophilized in a buffer solution with pH of 5.5 to 7

What is claimed is:

1. A method for quantitatively determining homocysteine in a biological specimen containing homocysteine and cysteine by use of an enzyme which is capable of forming hydrogen sulfide both from homocysteine and from cysteine, wherein the enzyme is O-acetyl homoserine lyase or L-methionine γ-lyase which comprises: (a) reacting the biological specimen with cysteine dioxygenase in the containing sodium chloride or ammonium sulfate and a sugar, in which cysteine dioxygenase is dissolved, before the reaction (a).

8. A reagent for quantitative determination of homocysteine, which comprises a reagent (I) containing cysteine dioxygenase, a reagent (II) containing a reducing agent and an enzyme which is capable of forming hydrogen sulfide both from homocysteine and from cysteine, wherein the enzyme is O-acetyl homoserine lyase or L-methionine γ-lyase and a reagent (III) containing metal ions and a metal indicator.

9. The reagent for quantitative determination of homocysteine according to claim 8, wherein the reducing agent is a thiol compound.

10. The reagent for quantitative determination of homocysteine according to claim 8, wherein the reagent (I) is obtained by dissolving cysteine dioxygenase in a buffer solution with pH of 5.5 to 7.

11. The reagent for quantitative determination of homocysteine according to claim 8, wherein the reagent (I) is obtained by dissolving cysteine dioxygenase in a buffer solution with pH of 5.5 to 7 containing sodium chloride or ammonium sulfate, and cryopreserving it.

12. The reagent for quantitative determination of homocysteine according to claim 8, wherein the reagent (I) is obtained by dissolving cysteine dioxygenase in a buffer solution with pH of 5.5 to 7 containing sodium chloride or ammonium sulfate and a sugar, and lyophilizing it.

13. The reagent for quantitative determination of homocysteine according to claim 8, wherein the enzyme is O-acetyl homoserine-lyase.

14. The reagent for quantitative determination of homocysteine according to claim 8, wherein the enzyme is L-methionine γ-lyase.

15. The method for quantitative determination of homocysteine according to claim 1, wherein the enzyme is O-acetyl homoserine-lyase.

16. The method for quantitative determination of homocysteine according to claim 1, wherein the enzyme is L-methionine γ-lyase.

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic DNA

<400> SEQUENCE: 1
ataccatgga acagaccgaa gtgct                                           25

<210> SEQ ID NO 2
<211> LENGTH: 31
<212> TYPE: DNA
<213> ORGANISM: Artificial Sequence
<220> FEATURE:
<223> OTHER INFORMATION: Synthetic DNA

<400> SEQUENCE: 2
ataaggatcc ttagttgttc tccagcgagc c                                    31
```